(12) United States Patent
McCarty (10) Patent No.: US 7,466,134 B2
(45) Date of Patent: Dec. 16, 2008

(54) METHOD AND APPARATUS FOR LOCATING UNDERGROUND CAST IRON PIPE JOINTS

(75) Inventor: Joe W. McCarty, Wauconda, IL (US)

(73) Assignee: Gas Technology Institute, Des Plaines, IL (US)

( * ) Notice: Subject to any disclaimer, the term of this patent is extended or adjusted under 35 U.S.C. 154(b) by 181 days.

(21) Appl. No.: 11/499,379

(22) Filed: Aug. 4, 2006

(65) Prior Publication Data
US 2008/0030189 A1   Feb. 7, 2008

(51) Int. Cl.
*G01V 3/11* (2006.01)
(52) U.S. Cl. ........................ 324/327; 324/326
(58) Field of Classification Search ........ 324/326–329, 324/228, 239, 243, 219–221; 166/250.01, 166/255.01, 66; 73/152.4
See application file for complete search history.

(56) References Cited

U.S. PATENT DOCUMENTS

| | | | |
|---|---|---|---|
| 3,823,365 A * | 7/1974 | Anderson | 324/328 |
| 4,091,322 A * | 5/1978 | Stankoff | 324/329 |
| 4,486,712 A * | 12/1984 | Weber | 324/329 |
| 4,507,608 A * | 3/1985 | Flach et al. | 324/220 |
| 5,617,031 A | 4/1997 | Tuttle | |
| 5,640,092 A | 6/1997 | Motazed et al. | |
| 5,650,725 A * | 7/1997 | Powell et al. | 324/326 |
| 5,729,143 A * | 3/1998 | Tavernetti et al. | 324/329 |

* cited by examiner

*Primary Examiner*—Reena Aurora
*Assistant Examiner*—Kenneth J Whittington
(74) *Attorney, Agent, or Firm*—Mark E. Fejer (57) ABSTRACT

An apparatus for locating underground cast iron pipe joints having an electrically driven resonant coil generating an alternating magnetic field and two resonant sensor coils disposed within the alternating magnetic field, each of the resonant sensor coils having an independent magnetic reluctance circuit. A device is provided for comparing electrical currents induced in each of the resonant sensor coils and a device is provided for indicating a relative magnitude of the electrical currents.

4 Claims, 6 Drawing Sheets

METHOD AND APPARATUS FOR LOCATING UNDERGROUND CAST IRON PIPE JOINTS

BACKGROUND OF THE INVENTION

1. Field of the Invention

This invention, in general, relates to a method and apparatus for locating hidden ferromagnetic objects. More particularly, this invention relates to a method and apparatus for locating underground ferromagnetic objects without excavation. More particularly yet, this invention relates to a method and apparatus for locating underground cast iron pipes and cast iron pipe joints employed in underground fluid distribution systems, such as natural gas pipelines.

2. Description of Related Art

Many water and gas utilities have distribution pipelines constructed of cast iron. With time, problems generally develop which cause fluid leakage. For example, in the case of gas utilities, seepage of gas from the bell and spigot joints connecting the pipe sections can occur. Technologies have been developed to seal these joints; however, to make the repairs requires excavation of the pipe. Thus, the ability to accurately locate the cast iron pipe joints is essential to maintaining the costs of excavation as low as possible.

New techniques enable the use of small diameter holes drilled from above ground to access the cast iron pipe joint. It will, thus, be apparent that reducing the number of holes required to be drilled in order to locate the cast iron pipe joint is a desirable objective. Accordingly, a device that is capable of accurately locating the joints may reduce or eliminate the boring of holes that miss the cast iron pipe joint target.

Many technologies, both active and passive, have been used in the past to determine the location of underground objects such as utility pipelines, power lines and the like. Among these technologies are nuclear, acoustic, gravitational, magnetic and electromagnetic methods and systems. Within the electromagnetic area of technology, infrared, microwave, low-frequency magnetic and eddy current devices have been employed.

A wide variety of metal detectors have also been used to locate buried objects, for geophysical exploration and for other applications as well. These devices typically operate to create a near field of continuous wave electromagnetic forces about a central inductive coil. Detection of a buried metallic object is evidenced by an impedance change. However, these devices are also sensitive to variations in the soil, resulting in numerous false positive signals. Many continuous electromagnetic wave type detectors are typically constructed of a transmit coil mutually coupled with a receiver coil. However, the requirement of mutually coupled coils inhibits the use and application of these types of devices. Because the geometry of the coils is critical for operation, the device must be constructed of rigid members to maintain precise relative coil placement. These types of devices are very sensitive to slight jarring or impact, which may cause coil movement, rendering the device inaccurate.

U.S. Pat. No. 5,617,031 to Tuttle teaches a buried pipe detection device based upon the principle of detecting differences in the dielectric/conductive properties of the ground in the vicinity of the pipe. The electrical properties of the ground directly over the buried pipe are said to differ from those in an area immediately adjacent to the pipe. The device employs a capacitor plate array that injects a low frequency sinusoidal signal into the ground and samples the injected signal from two spatially separated locations of the array.

U.S. Pat. No. 5,640,092 to Motazed et al. teaches an electromagnetic pipe mapper for determining the location and depth of buried pipes. The device includes a target signal transmitter for inducing an electromagnetic signal in the buried object, a position reference transmitter for transmitting a signal for positioning purposes, a sensor unit for detecting changes in the magnetic flux of the buried object due to the induced electromagnetic signal and the positioning signal from the position reference transmitter, and a central unit for processing and displaying a map of the buried object.

Although, as evidenced by the above referenced U.S. patents, devices exist for locating buried pipe, none of these known devices is able to detect buried pipe joints or other buried pipeline features.

SUMMARY OF THE INVENTION

Accordingly, it is one object of this invention to provide a method and apparatus capable of accurately locating without excavation underground cast iron pipes.

It is another object of this invention to provide a method and apparatus capable of locating without excavation the cast iron pipe joints of the underground cast iron pipes.

It is yet a further object of this invention to provide a method and apparatus for locating without excavation other features of underground cast iron pipes.

These and other objects of this invention are addressed by an apparatus for locating underground cast iron pipe joints comprising an electrically driven resonant coil generating an alternating magnetic field, two resonant sensor coils disposed within the alternating magnetic field, each of which is provided with an independent magnetic reluctance circuit, means for comparing electrical currents induced in each of the resonant sensor coils, and means for indicating a relative magnitude of the electrical currents.

It will be understood by those skilled in the art that the method and apparatus of this invention are capable not only of locating the cast iron pipe joints of underground fluid distribution systems, but also may be used to locate any underground ferromagnetic objects in close proximity to the surface, less than about 6 feet deep. As used herein, the term "ferromagnetic" refers to a material with high magnetic permeability, that is, a material that imposes little resistance to orientation in the presence of a magnetic field. Materials such as iron, steel, and nickel are ferromagnetic substances. It will also be understood that the method and apparatus of this invention, broadly speaking, are capable of locating most any hidden ferromagnetic objects, whether above or below ground, and such applications are deemed to be within the scope of this invention.

In operation, an oscillating electrical current is passed through the electrically driven resonant coil, forming an oscillating magnetic field. An electrical current is induced in each of the two resonant sensor coils disposed within the oscillating magnetic field. The magnetic reluctance between the electrically driven resonant coil and each of the resonant sensor coils representative of the absence of an underground ferromagnetic object or cast iron pipe joint is measured, producing an initial magnetic reluctance. Ferromagnetic material in the vicinity produces changes in the magnetic reluctance circuit between the drive coil and the sensor coils. As the magnetic reluctance changes, the amplitude and phase of induced currents in the sensor coils changes. This change in the phase and amplitude of the induced sensor coil constitutes proximity to a ferromagnetic object. By subtracting the induced signals produced by each of the sensor coils and using a phase reference signal from the drive coil oscillator a null output is produced in the absence of ferromagnetic material in the vicinity. The linear arrangement of the coils allow them to be aligned parallel with the linear pipe of uniform cross-section and produce a null output. A change in the cross-section (a joint) unbalances the two reluctance circuits, the induced currents and produces a non-null output signal. A drive coil and one sensor coil is capable of detecting ferromagnetic materials in the vicinity. It is the use of two sensor coils in a line with the drive coil in the center and the null response to a uniform cross-section pipe that enables the detection of joints by this invention. The magnetic reluctance is then measured while moving the coils, whereby a measured magnetic reluctance substantially different from the initial magnetic reluctance constitutes proximity to the underground ferromagnetic object or cast iron pipe joint.

BRIEF DESCRIPTION OF THE DRAWINGS

These and other objects and features of this invention will be better understood from the following detailed description taken in conjunction with the drawings wherein.

DETAILED DESCRIPTION OF THE PRESENTLY PREFERRED EMBODIMENTS

Although discussed herein in connection with the location of underground cast iron pipes and cast iron pipe joints, it is to be understood that the method and apparatus of this invention may be applied to the determination of the location of any hidden or obscured ferromagnetic material, including buried ferromagnetic material and ferromagnetic material disposed in or behind the walls of structures, and such applications are considered to be within the scope of this invention.

Figure 1:
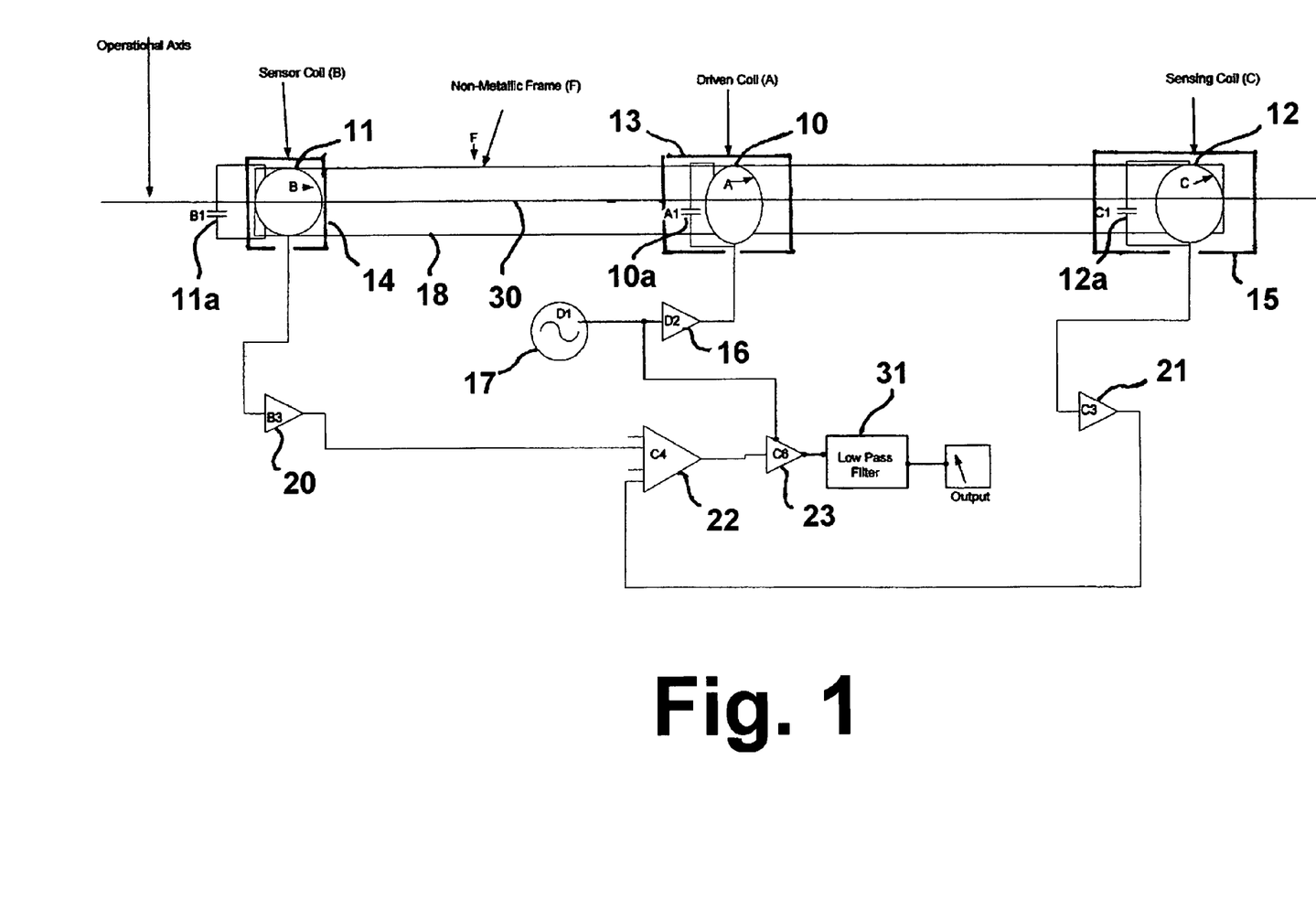
FIG. 1 is a circuit diagram for the cast iron pipe joint locator in accordance with one embodiment of this invention.

Referring to FIG. 1, the apparatus of this invention comprises an electrically driven resonant coil 10 and two resonant sensor coils 11, 12. Each of the coils is tuned to an electrically resonant frequency by means of a parallel capacitor, 10a, 11a, 12a connected with a corresponding coil. That is, parallel capacitor 10a is connected with electrically driven resonant coil 10, parallel capacitor 11a is connected with resonant sensor coil 11, and parallel capacitor 12a is connected with resonant sensor coil 12. In accordance with one embodiment of this invention, each of the resonant coils 10, 11, 12 is surrounded by a conductive electrostatic shield 13, 14, 15, each shield having an insulating break to prevent the shield from acting as a shortened secondary turn. In accordance with one embodiment of this invention, resonant sensor coils 11, 12 are shielded and no shield is used with the electrically driven resonant coil 10. In accordance with one embodiment of this invention, aluminum foil may be employed as an electrostatic shield. In accordance with another embodiment of this invention, the electrostatic shield may be a single-sided copper clad printed circuit material with a hole in the center. A break in the ring of copper foil is created to avoid the shorted turn problem. In accordance with one embodiment of this invention, an electrostatic shield is disposed above and below each resonant sensor coil with at least a 0.25 inch spacing between the coil and the shield. Signal strength may be altered by altering the distance between the coils and the shields.

The electrically driven resonant coil 10 is connected by a coaxial cable with the output of amplifier 16, the input of which is connected with oscillator 17. Amplifier 16 and oscillator 17 are tuned to the electrical resonant frequency of electrically driven resonant coil 10 and capacitor 10a. Resonant sensor coils 11, 12 are maintained in the same plane as electrically driven resonant coil 10 by a non-magnetic frame 18. Resonant sensor coils 11, 12 are disposed on opposite-sides of electrically driven resonant coil 10 and, in accordance with one preferred embodiment of this invention, are equidistant therefrom. A line 30 through the centers of all three resonant coils 10, 11, 12 forms the operational axis of the apparatus. Electrical signals from each of the resonant sensor coils 11, 12 are provided through separate coaxial cables connecting them with amplifiers 20, 21. The outputs of amplifiers 20, 21 are subtracted and amplified by amplifier 22, the inputs of which are connected with the outputs of amplifiers 20, 21. The output of amplifier 22 is connected with the input of lock-in amplifier 23, which processes the output signal of amplifier 22 using a reference signal from oscillator 17. A low pass filter 31 connected with the output of lock-in amplifier 23 produces a DC voltage proportional to the amplitude and phase differences between the electrical signals from resonant sensor coils 11, 12.

In operation, an oscillating current is introduced into electrically driven resonant coil 10, producing an oscillating magnetic field. The oscillating magnetic field, in turn, induces electrical currents in resonant sensor coils 11, 12. In the absence of nearby ferromagnetic materials, the magnet reluctance between electrically driven resonant coil 10 and resonant sensor coil 11 and between electrically driven resonant coil 10 and resonant sensor coil 12 are substantially equal. Under this condition, the output voltage of lock-in amplifier 23 has a near zero value. If the ferromagnetic material is brought within the range of coils 10, 11, 12, the magnetic reluctance between the coils will be altered. As the ferromagnetic object moves along a line parallel to the operational axis of the apparatus of this invention, the output of lock-in amplifier 23 will change as shown in FIG. 2.

Figure 5:
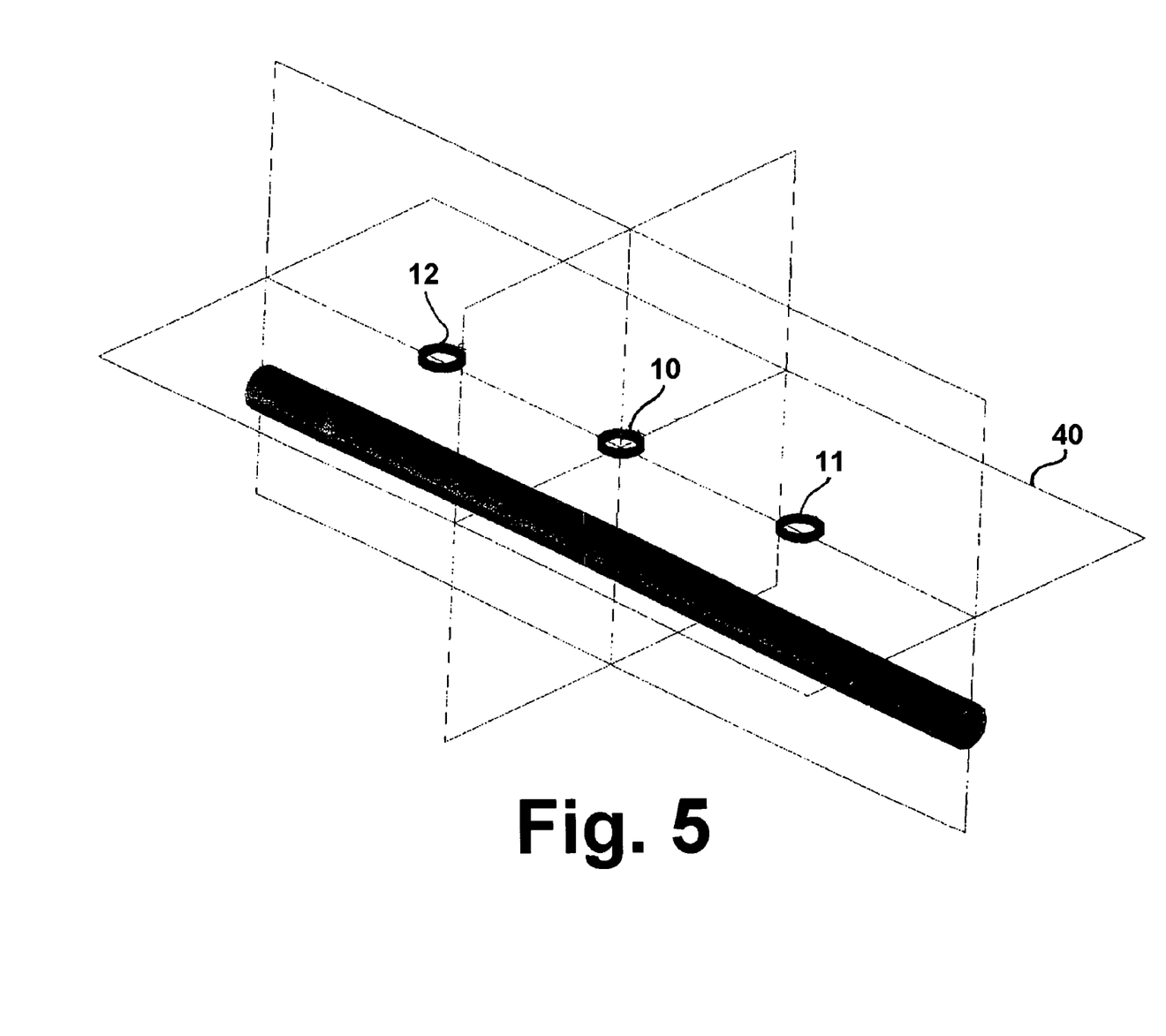
FIG. 5 is a diagram showing the orientation relative to the cast iron pipe of the coils of the apparatus of this invention for locating cast iron pipe joints.

As previously indicated, the operational axis of the apparatus of this invention is a line connecting the centers of the coils 10, 11, 12 as shown in FIG. 1. The horizontal plane 40 formed by the coils along the operational axis, as shown in FIG. 5, is held parallel to the ground during use of the apparatus. If the device is moved over the ground and the operational axis of the apparatus is perpendicular to the disposition of the buried pipe, the output signal of the apparatus will increase from zero, decrease, pass through zero, decrease and then increase back to zero. If the direction of travel across the pipe is reversed, the output sequence will be reversed.

Figure 2:
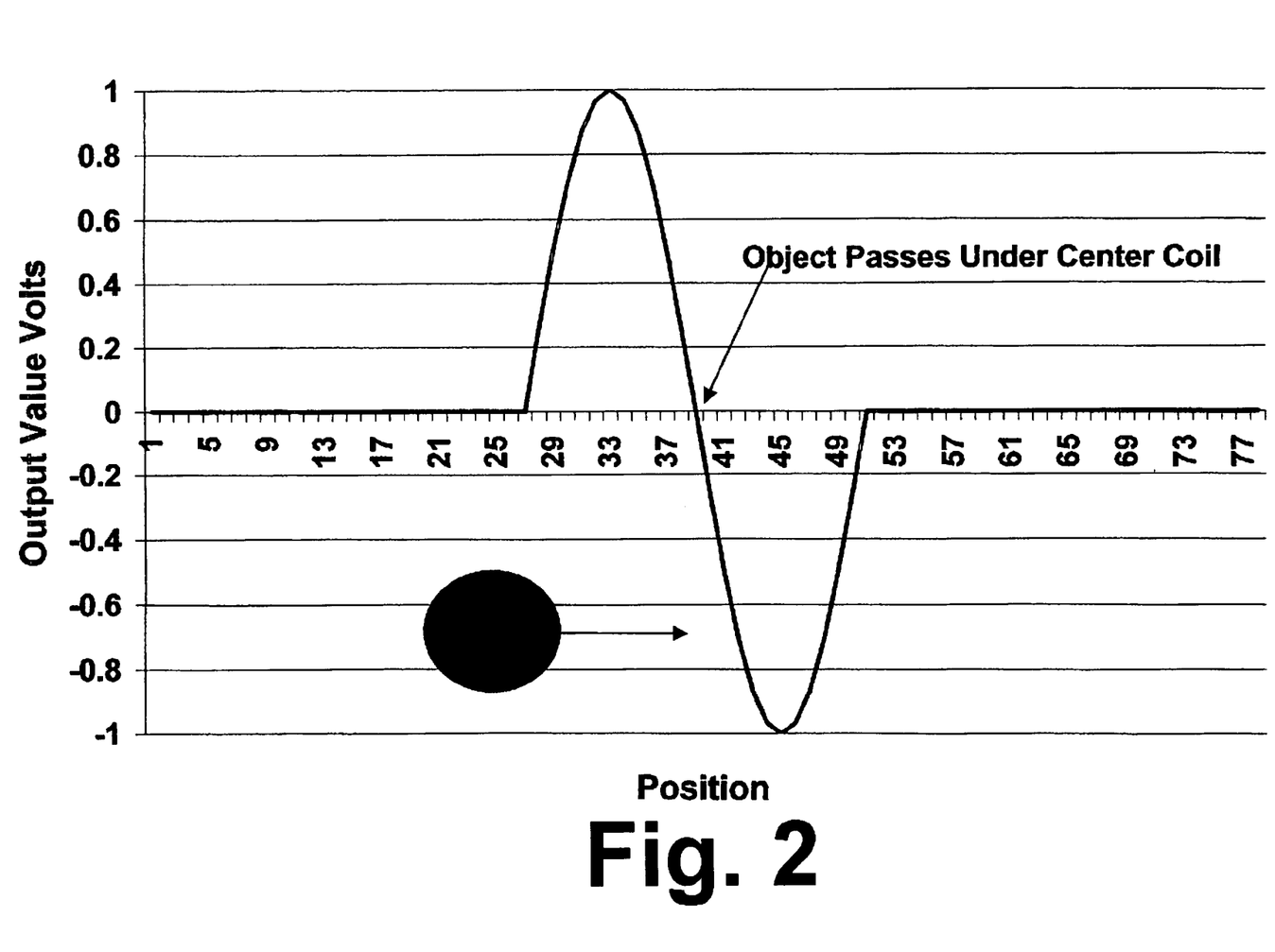
FIG. 2 is a graphical representation demonstrating the changes that occur in magnetic reluctance, expressed in volts, as the apparatus of this invention is brought into close proximity with the underground ferromagnetic object to be located.

FIG. 2 shows the output voltage of the apparatus of this invention as a function of the distance from a long cylindrical object such as a ferromagnetic pipe. The length of the pipe is perpendicular to the operational axis of the apparatus. As shown, the output voltage is about zero when the apparatus is at a substantial distance from the pipe. As the apparatus approaches the pipe, the output signal changes. When one of the resonant sensor coils is closest to the pipe, the output voltage is positive whereas when the other resonant sensor is closest to the pipe, the output signal is negative. In the case where electrically driven resonant coil 10 is directly over the pipe and the distances between the resonant sensor coils and the pipe are substantially equal, the magnetic reluctance paths are balanced and the output voltage returns to zero.

Figure 3:
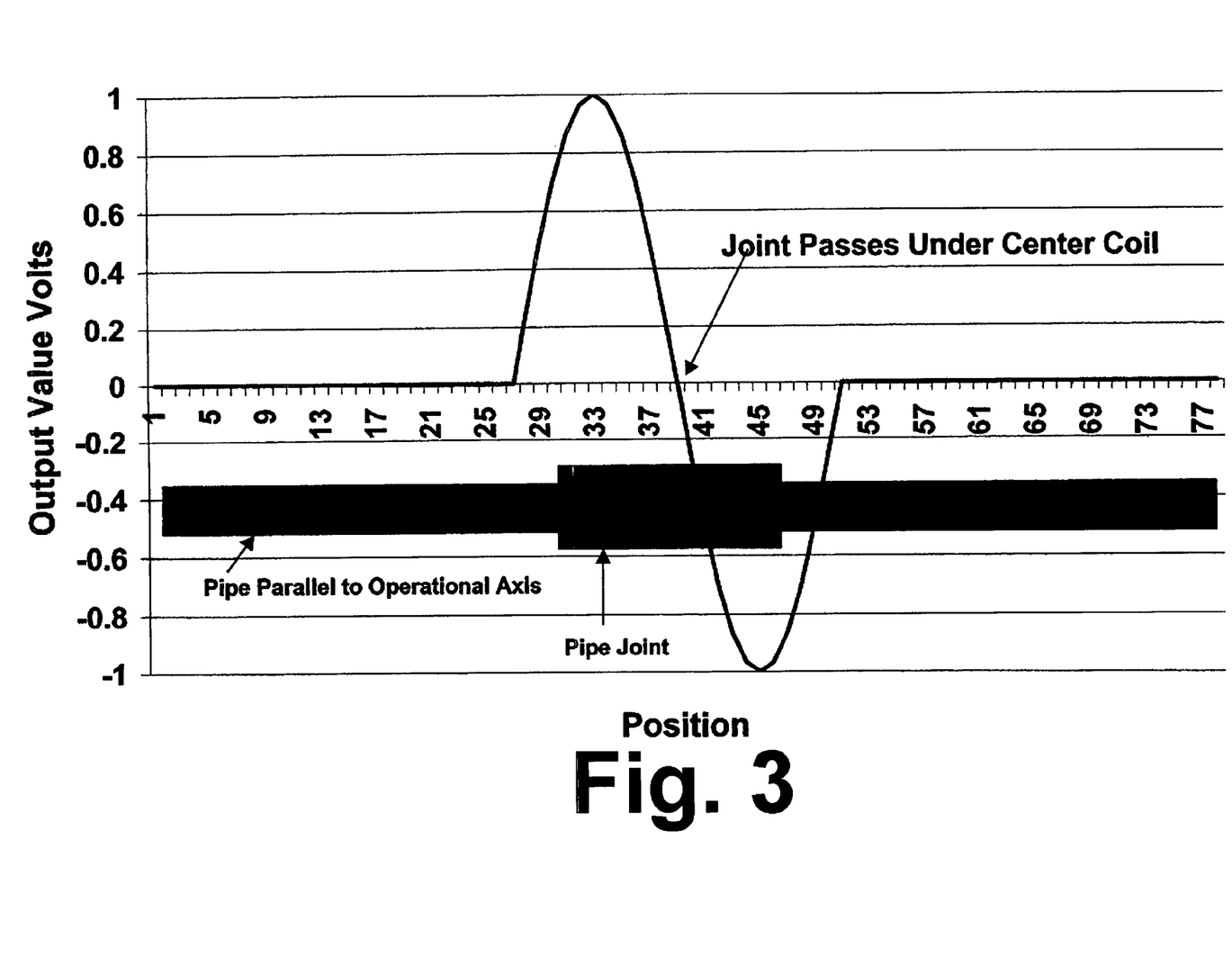
FIG. 3 is a graphical representation demonstrating the changes that occur in magnetic reluctance, expressed in volts, as the apparatus of this invention is brought into close proximity with an underground cast iron pipe joint.

If the apparatus of this invention is moved above ground and the operational axis of the apparatus is parallel to a buried pipe of substantially uniform cross-section as shown in FIG. 5, little or no change will be seen in the output of the device until a change in the uniform cross-section of the pipe occurs, producing a change in the apparatus output. FIG. 3 shows the output voltage for the apparatus of this invention as a function of distance as the apparatus is moved parallel to a cast iron pipe having non-uniform cross-sections, such as occurs at bell and spigot joints, valves, welds, and the like. As long as the cross-section of the pipe is uniform, the magnetic reluctance paths are equal and the output voltage remains at or close to zero. If the cross-section of the pipe changes, such as occurs at bell and spigot joints, etc., the magnetic reluctance paths will no longer be equal and the output voltage will change in relation to the distance of the apparatus from the change in cross-section.

Figure 4:
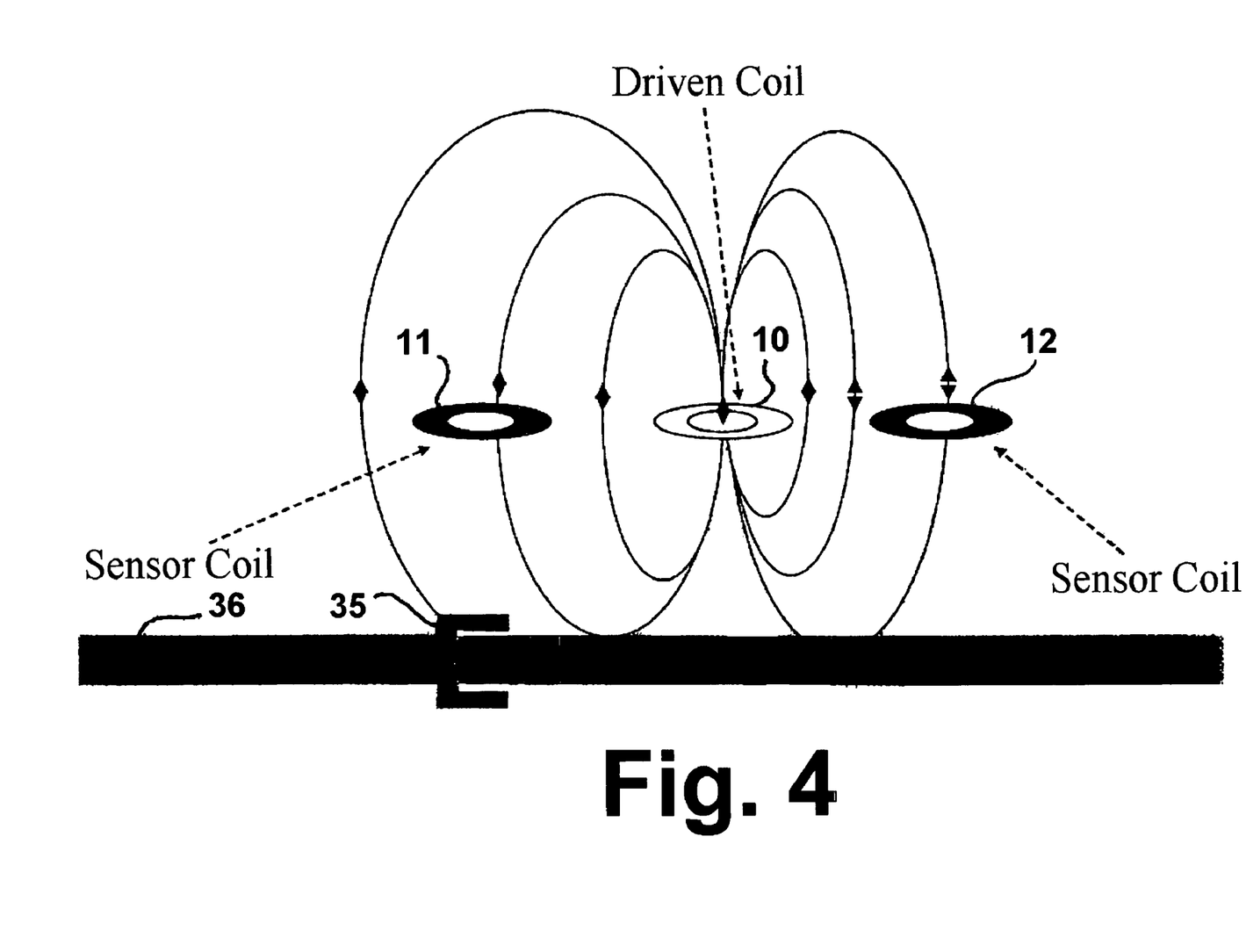
FIG. 4 is a diagram showing the basic principle of the method and apparatus of this invention.

FIG. 4 shows the basic operating principle for the apparatus of this invention. With the electrically driven resonant coil 10 disposed between two resonant sensor coils 11, 12, the magnet reluctance associated with the resonant sensor coil 11 upon coming into close proximity with the "extra metal" 35 of an underground pipe 36 increases relative to the magnetic reluctance of the resonant sensor 12 distal from the "extra metal."

It will also be appreciated by those skilled in the art that determination of the location of a hidden ferromagnetic object in accordance with the method and apparatus of this invention, while employing preferred dispositions of the operational axis of the apparatus as discussed herein above relative to the hidden ferromagnetic object, does not require such relative disposition. Thus, while the preferred disposition of the operational axis of the apparatus for locating an underground cast iron pipe is perpendicular to the pipe, other dispositions, e.g. parallel to the underground pipe, may be employed. In these cases, proximity to the underground ferromagnetic pipe will result in a general spike in the measured magnetic reluctances.

The output signal of the apparatus of this invention is similar in shape for either a perpendicular pipe crossing or when passing over a joint or when the apparatus is parallel to the pipe. The operator must first locate the path of the pipe in order to move the device parallel to the pipe to detect joints. To distinguish between the crossing of two pipes and a joint, the apparatus is moved parallel to the pipe but a few feet to one side of the traverse over the pipe. A crossing pipe will produce a signal; a joint on the first pipe will produce a reduced signal or no signal depending on the distance of the second traverse. Perpendicular traverses over joints will produce a larger output swing than perpendicular traverses over the uniform cross-sectioned pipe.

EXAMPLE

Figure 6:
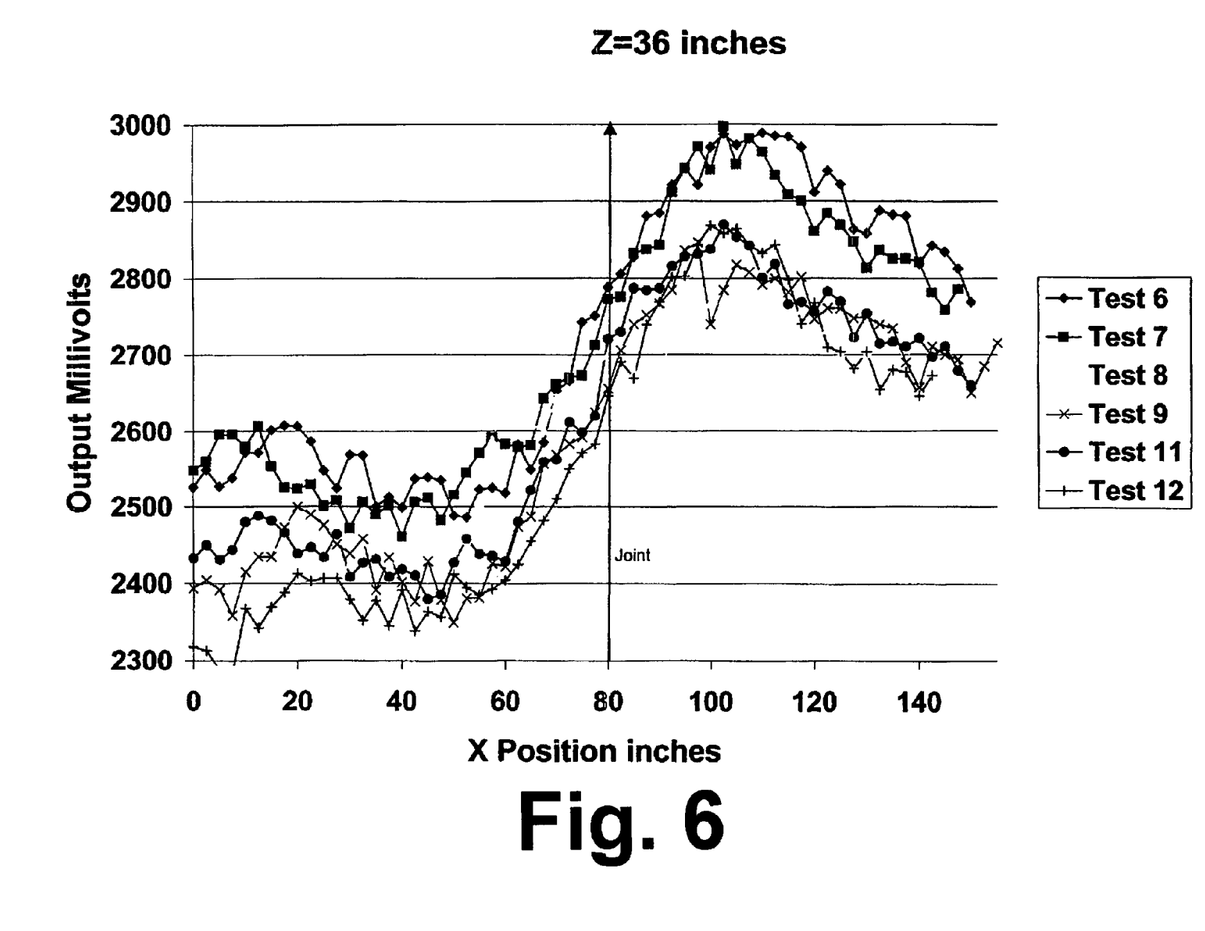
FIG. 6 is a graphical depiction showing the results from several tests of the apparatus of this invention.

A laboratory version of the apparatus of this invention was constructed using 83 kHz coils 8 inches in diameter. Aluminum foil was used as the electrostatic shielding on the coils. A 1 MHz crystal oscillator and a divide by 6 counter were used to drive two D-edge flip-flops. The output of the flip-flop circuits produced 83 kHz square waves with 0, 90, 180, and 270-degree phase shifts. The zero degree signal was used to trigger a logic FET used to drive the electrically driven resonant coil. The 0, 90, 180 and 270 degree phase signals were tried as inputs to the detector circuits. The signal from each of the resonant sensor coils 11, 12 were sent through high impedance voltage following amplifiers. The outputs of the amplifiers were connected to the inputs of a differential input instrumentation amplifier. The output of the instrumentation amplifier was further amplified and sent to demodulator/phase detector circuits. Two circuits, a balanced demodulator and a phase detector, were tried with comparable results. The balanced demodulator was used as a lock-in amplifier. The balanced demodulator circuit used both phase and amplitude information but was most sensitive to target movement when the input signals were large enough to drive the amplifiers into clipping. The phase detector circuit was used to minimize the effects of amplitude on the ability to detect targets. The phase detector used a comparator to convert the sine wave output of the sensor coil amplifier system into square waves containing only the phase information. An exclusive-or gate was used to compare the phases of the sensor coil signal to one of the phases, 0, 90, 180, and 270-degrees used to drive the electrically driven resonant coil. The output of the exclusive-or gate was buffered and a copy of the signal was inverted. The buffered and inverted signals were passed through low-pass filters and then amplified by a differential amplifier. The resulting signal was viewed both on an oscilloscope and a digital meter. The apparatus was tested using pipe laying on the floor a the laboratory, moving the apparatus relative to the pipe and recording the voltage output of the apparatus. The results of these tests are shown in FIG. 6.

It will be apparent that there exist numerous configurations for the apparatus of this invention. By way of example, a PIC microprocessor may be used to generate the 83 kHz square wave. A square wave with a duty cycle of 25% produces the largest output. In accordance with one embodiment of this invention, the voltage-following amplifiers for each sensor coil may be mounted within the coils so as to reduce noise. In accordance with another embodiment of this invention, an Analog Devices AD630 Balanced Modulator/demodulator amplifier may be used to combine the two sensor coil signals and demodulate them using a reference signal from the PIC microprocessor. The Analog Devices AD630 Balanced Modulator Demodulator is used as a lock-in amplifier. This embodiment did not result in clipping of the signals but used both the phase and amplitude of the signals from the sensor coils. The output of the AD630 Balanced Modulator/demodulator amplifier may be passed through a low pass filter and transmitted to both a digital voltmeter display and an analog input on the PIC microprocessor. In accordance with one embodiment of this invention, the coils and electronics may be mounted in a wooden frame to avoid extraneous signals produced by the movement of coaxial cables used to connect the sensor coils to the AD630 circuitry. In accordance with one embodiment, four 6-inch diameter wheels may be attached to the wooden frame. Eight magnets are then glued to one of the wheels spaced so that as the wheel turns, the magnets pass a digital Hall effect sensor resulting in the generation of a pulse for each 2.52 inches of travel by the frame over the ground. The output of the Hall effect sensor may be sent to the PIC microprocessor. In accordance with one embodiment of this invention, the PIC microprocessor may be programmed to generate the 83 kHz square wave signal and to record the analog input from the AD630 circuits when a magnet on the wheel triggers the Hall effect sensor. The analog reading may be recorded in Flash memory for later transfer to a laptop computer. This digital recording of the signal allows for faster collection of information and avoids signal drift that may occur when data are collected over longer periods of time.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. A method for locating underground cast iron pipe joints comprising the steps of:
   determining the location and orientation of an underground cast iron pipe;
   passing an oscillating electrical current through an electrically driven resonant coil disposed substantially vertically above said underground cast iron pipe, forming an oscillating magnetic field;
   inducing an electrical current in each of two resonant sensor coils disposed within said oscillating magnetic field;
   measuring a magnetic reluctance between said electrically driven resonant coil and each of said resonant sensor coils, producing an initial magnetic reluctance; and
   measuring said magnetic reluctance while moving said coils above and parallel to said cast iron pipe, whereby measured magnetic reluctances substantially different from said initial magnetic reluctance constitutes proximity to a cast iron pipe joint.

2. A method in accordance with claim 1, wherein said resonant sensor coils are aligned with said electrically driven resonant coil and disposed on opposite sides of said electrically driven resonant coil.

3. A method in accordance with claim 1, wherein said resonant sensor coils are equidistant from said electrically driven resonant coil.

4. A method in accordance with claim 1, wherein said electrically driven resonant coil and said resonant sensor coils are in a same plane.

* * * * *